(12) United States Patent
Engel

(10) Patent No.: US 6,705,920 B1
(45) Date of Patent: Mar. 16, 2004

(54) BREAST PUMP HOLDING STRAP

(76) Inventor: Julie Engel, 204 W. Craig, San Antonio, TX (US) 78212

( * ) Notice: Subject to any disclaimer, the term of this patent is extended or adjusted under 35 U.S.C. 154(b) by 56 days.

(21) Appl. No.: 10/185,214

(22) Filed: Jun. 28, 2002

(51) Int. Cl.[7] ................................................ A41C 3/00
(52) U.S. Cl. .......................... 450/36; 2/338; 604/346
(58) Field of Search .............................. 450/36, 37, 1, 450/7–10, 58.79, 82–84; 2/336, 338, 311–312; 604/346, 73–75; 128/890; 119/852

(56) References Cited

U.S. PATENT DOCUMENTS 1,094,158 A * 4/1914 Mattson ........................ 450/36
6,004,186 A * 12/1999 Penny .......................... 450/36
6,027,396 A * 2/2000 Yonchar ....................... 450/36
6,213,840 B1 * 4/2001 Han ............................. 450/36
6,227,936 B1 * 5/2001 Mendoza ...................... 450/36

* cited by examiner

Primary Examiner—Gloria M. Hale

(57) ABSTRACT

A breast milk pump holding strap that includes two elastic bands that are adjustably securable to each other with a pair of companionate hook and pile fasteners along the back and front thereof to form a closed loop and that each include a slit through which a narrow portion of the cone of the breast pump is positioned prior to positioning of the straps in place such that each cone is held over a respective breast of the user.

1 Claim, 1 Drawing Sheet

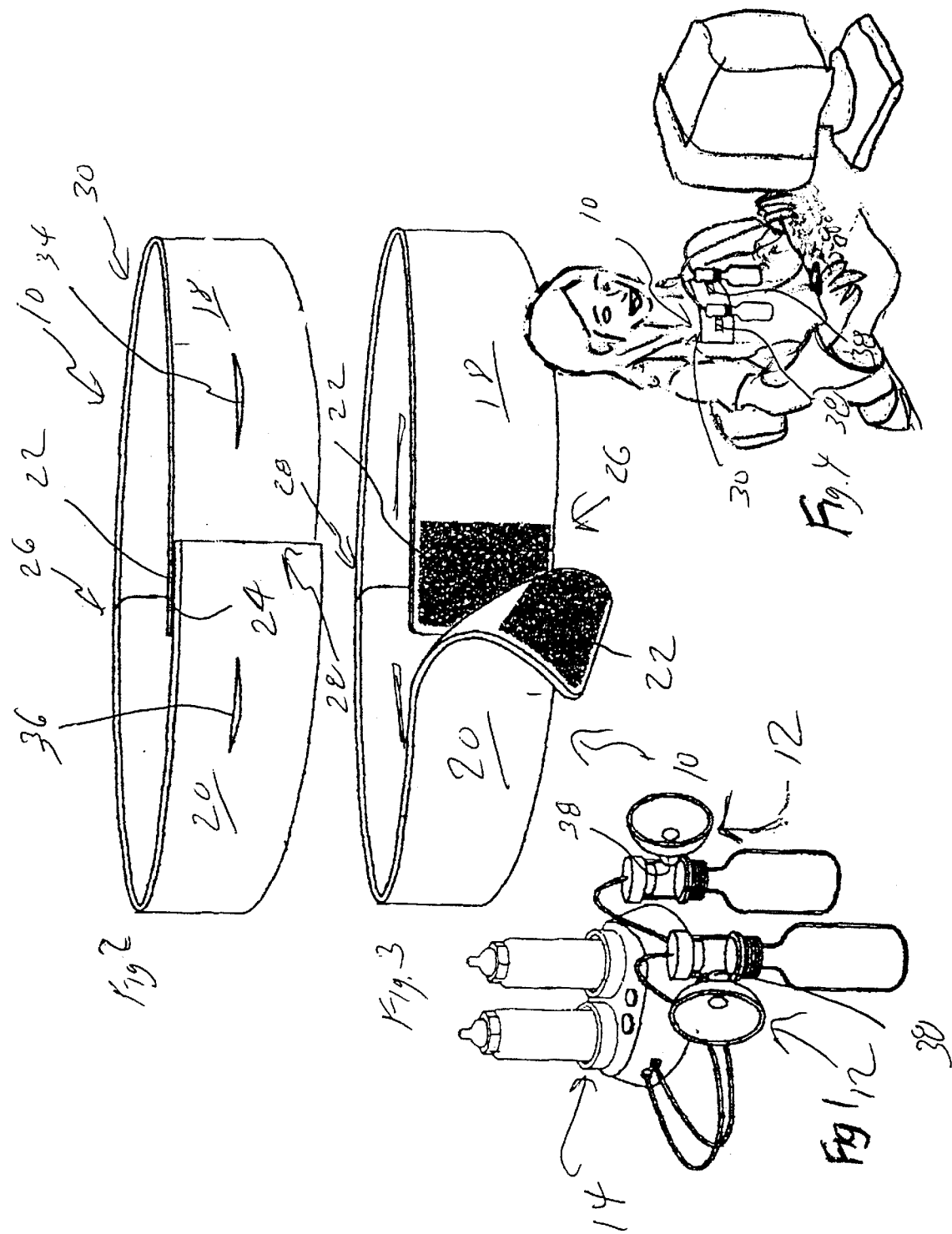

BREAST PUMP HOLDING STRAP

TECHNICAL FIELD

The present invention relates to support structures and more particularly to a breast milk pump holding strap for holding the holding cones of a breast milk pump of the type which include a holding cone that is positioned over the breast and in connection with a collecting tube; the breast pump holding strap including two elastic bands that are adjustably securable to each other with a pair of companionate hook and pile fasteners along the back and front thereof to form a closed loop and that each include a slit through which a narrow portion of the cone of the breast pump is positioned prior to positioning of the straps in place such that each cone is held over a respective breast of the user.

BACKGROUND ART

It is often uncomfortable or bothersome for women who are breast feeding to pump milk as the process can be a time consuming chore. It would be desirable, therefore, to have a structure for supporting the cone of the breast milk in place so that the hands of the user would be available for performing other activities while breast milk was being collected.

GENERAL SUMMARY DISCUSSION OF INVENTION

It is thus an object of the invention to provide a breast milk pump holding strap that includes two elastic bands that are adjustably securable to each other with a pair of companionate hook and pile fasteners along the back and front thereof to form a closed loop and that each include a slit through which a narrow portion of the cone of the breast pump is positioned prior to positioning of the straps in place such that each cone is held over a respective breast of the user.

Accordingly, a breast milk pump holding strap is provided. The breast milk pump holding strap includes two elastic bands that are adjustably securable to each other with a pair of companionate hook and pile fasteners along the back and front thereof to form a closed loop and that each include a slit through which a narrow portion of the cone of the breast pump is positioned prior to positioning of the straps in place such that each cone is held over a respective breast of the user.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein:

FIG. 1 is a perspective view of a representative breast milk pump including cones positionable over the breast of the user.

FIG. 2 is a front perspective view of the exemplary embodiment of th breast milk pump holding strap of the present invention FIG. 3 is a back perspective view of the breast milk pump holding strap.

FIG. 4 shows the exemplary embodiment of the breast milk pump holding strap in use with representative breast milk pump system.

EXEMPLARY MODE FOR CARRYING OUT THE INVENTION

FIGS. 1–4 show various aspects of an exemplary embodiment of the breast milk pump holding strap of the present invention generally designated 10. Breast milk pump holding strap 10 is adapted for holding the cones 12 of representative breast milk pump 14. Holding strap 10 includes two elastic bands 18, 20 that are adjustably securable to each other with a pair of companionate hook and pile fasteners 22, 24 along the back 26 and front 28 thereof to form a closed loop, generally designated 30. Each band 18, 20 includes a slit 34, 36 through which a narrow portion 38 of the cone 12 of the breast pump 14 is positioned prior to positioning of the strap 10 in place such that each cone 14 is held over a respective breast of the user.

It can be seen from the preceding description that a breast milk pump holding strap has been provided.

It is noted that the embodiment of the breast milk pump holding strap described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A breast milk pump holding strap for holding the holding cones of a breast milk pump of the type which include a holding cone having a narrow portion in connection with a collecting tube and a breast cone portion that is positioned over a breast during operation of the breast milk pump; the breast milk pump holding strap comprising:

two elastic bands that are adjustably securable to each other with a pair of companionate hook and pile fasteners along the back and front thereof to form a closed loop and that each include a slit through which a narrow portion of a holding cone of a breast milk pump is positioned prior to securing the back and front ends of the two elastic bands together to form a closed loop about the user such that each holding cone having a narrow portion inserted through the slit of one of the two elastic bands has the corresponding breast cone portion thereof secured over a breast of the user.

* * * * *